US008809573B2

(12) United States Patent
Armitage et al.

(10) Patent No.: US 8,809,573 B2
(45) Date of Patent: *Aug. 19, 2014

(54) CARBONYLATION PROCESS

(75) Inventors: Gareth Gerald Armitage, York (GB);
Bogdan Costin Gagea, Hull (GB);
David John Law, Beverley (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 149 days.

This patent is subject to a terminal disclaimer.

(21) Appl. No.: 13/138,991

(22) PCT Filed: May 6, 2010

(86) PCT No.: PCT/GB2010/000916
§ 371 (c)(1),
(2), (4) Date: Nov. 9, 2011

(87) PCT Pub. No.: WO2010/130972
PCT Pub. Date: Nov. 18, 2010

(65) Prior Publication Data
US 2012/0078005 A1 Mar. 29, 2012

(30) Foreign Application Priority Data
May 14, 2009 (EP) ..................... 09251311

(51) Int. Cl.
*C07C 67/37* (2006.01)
*C07C 57/08* (2006.01)
*C07C 51/12* (2006.01)
*B01J 29/18* (2006.01)
(52) U.S. Cl.
CPC .................. *C07C 51/12* (2013.01); *B01J 29/18* (2013.01); *B01J 2229/36* (2013.01); *B01J 2229/16* (2013.01); *B01J 2229/38* (2013.01); *C07C 67/37* (2013.01)
USPC ................. 560/232; 502/25; 502/78
(58) Field of Classification Search
CPC ...................................................... C07C 67/36
USPC ....................................... 560/232; 502/25, 78
See application file for complete search history.

(56) References Cited

U.S. PATENT DOCUMENTS

| | | | |
|---|---|---|---|
| 3,326,797 A | 6/1967 | Young et al. | |
| 3,374,182 A | 3/1968 | Young et al. | |
| 3,551,353 A | 12/1970 | Chen et al. | |
| 5,118,482 A | 6/1992 | Narayana et al. | |
| 5,238,677 A | 8/1993 | Apelian et al. | |
| 6,184,167 B1 | 2/2001 | Van Mao et al. | |
| 2012/0053360 A1* | 3/2012 | Ditzel et al. | 560/232 |
| 2012/0101298 A1* | 4/2012 | Ditzel et al. | 560/206 |

FOREIGN PATENT DOCUMENTS

| | | |
|---|---|---|
| CN | 101613274 A | 12/2009 |
| EP | 1 985 362 A1 | 10/2008 |
| EP | 2 014 619 A2 | 1/2009 |
| EP | 2 085 375 A1 | 8/2009 |
| WO | WO 2006/121778 A1 | 11/2006 |
| WO | WO 2007/041851 A1 | 4/2007 |
| WO | WO 2007/128955 A1 | 11/2007 |
| WO | WO 2008/147190 A1 | 12/2008 |

OTHER PUBLICATIONS

Li, Xianfeng, et al; "Synthesis and characterization of mesoporous mordenite"; *Journal of Catalysis*, 262; 257-265 (2009).
van Donk, S., et al; "Combined Diffusion, Adsorption, and Reaction Studies of n-Hexane Hydroisomerization over Pt/H-Mordenite in an Oscillating Microbalance"; *Journal of Catalysis*, 204, 272-280 (2001).
Boveri, M., et al; "Steam and acid dealuminatino of mordenite Characterization and influence on the catalytic performance in linear alkylbenzene synthesis"; *Catalysis Today*, 114, 217-225 (2006).
Moolenaar, R.J., et al; "The Structure of the Aluminate Ion in Solutinos at High pH"; *The Journal of Physical Chemistry*, vol. 74, No. 20, 3629-3636 (1970).
Groen, J.C., et al; "On the introduction of intracrystalline mesoporosity in zeolites upon desilicatin in alkaline medium"; *Microporous and Mesoporous Materials*; 69, 29-34 (2004).
Groen, J.C., et al; "Alkaline Posttreatment of MFI Zeolites, From Accelerated Screening to Scale-up"; *Ind. Eng. Chem. Res.*; 46, 4193-4201 (2007).
Groen, J.C., et al; "Mesoporous beta zeolite obtained by desilication"; *Microporous and Mesoporous Materials*; vol. 114, Issues 1-3, 93-102 (Sep. 2008).
Groen, J.C., et al; "Alkaline-mediated mesoporous mordenite zeolites for acid-catalyzed conversions"; *DelftChemTech*, Delft University of Technology, Julianalaan 136, 2628 BL Delft, The Netherlands, (18 pgs), Received Jun. 7, 2007; revised Jul. 11, 2007; accepted Jul. 13, 2007. Available online Aug. 24, 2007.
Groen, J.C., et al; "Mechanism of Hierarchical Porosity Development in MFI Zeolites by Desilication: The Role of Aluminium as a Pore-Directing Agent"; *Chem. Eur. J.*, 11, 4983-4994 (2005).
Yang, X., et al; "Observation and study of new tetrahedral Al sites in $NH_3$-treated, steamed zeolites using MAS $^{27}$ Al and $^{15}$N n.m.r."; *Zeolites*; 16, 249-253 (1996).
Zhang, Y., et al; "Vapor phase Beckmann rearrangement of cyclohexanone oxime on Hβ-zeolites treated by ammonia"; *Microporous and Mesoporous Materials*, 107, 247-251 (2008).
PCT International Preliminary Report on Patentability dated Nov. 25, 2011; International Application No. PCT/GB2010/000916, International Filing date May 6, 2010 (7 pgs).

* cited by examiner

*Primary Examiner* — Yong Chu
(74) *Attorney, Agent, or Firm* — Nixon & Vanderhye, P.C.

(57) ABSTRACT

A process for the production of acetic acid and/or methyl acetate by the carbonylation of methanol, methyl acetate and/or dimethyl ether with carbon monoxide in the presence of a desilicated mordenite catalyst.

15 Claims, No Drawings

CARBONYLATION PROCESS

This application is the U.S. national phase of International Application No. PCT/GB2010/000916 filed 6 May 2010 which designated the U.S. and claims priority to European Application No. 09251311.8 filed 14 May 2009, the entire contents of each of which are hereby incorporated by reference.

This invention relates to a process for the carbonylation of methanol and/or reactive derivatives thereof in the presence of a desilicated mordenite catalyst.

Mordenite is known to be used as a catalyst in numerous hydrocarbon conversion processes, such as cracking, (hydro) isomerisation and the alkylation of aromatic compounds. The improvement of the catalytic performance of mordenite in such hydrocarbon conversion reactions has been the subject of several research investigations. The use of sodium hydroxide to desilicate a non-dealuminated mordenite is described in WO 2008/147190. The treated mordenite was shown to exhibit improved catalytic performance in the alkylation of benzene.

The catalytic behaviour of mesoporous mordenites in the isomerisation of 2-methyl-2-pentene and the alkylation of benzene was studied in Xianfeng et al, Synthesis and characterisation of mesoporous mordenite, Journal of Catalysis 262 (2009) 257-265. The mesoporous mordenites were prepared by treating mordenite with sodium hydroxide and/or nitric acid. It was found that in the isomerisation reaction, the conversion of 2-methyl-2-pentene over the untreated mordenite was superior to that over the acid treated mordenite. The conversion of benzyl alcohol in the benzylation of benzene over the untreated and acid treated mordenites were both less than 3%. The alkylation reaction results were reported to be different to the isomerisation reaction results due to the differences in the nature of the reactions.

In general, results from treatments of zeolites with acid and/or bases cannot be extrapolated directly from one zeolite type to another zeolite type or from one reaction type to a different reaction type.

Mordenite has been disclosed for use as a catalyst in the gas phase carbonylation of methanol and/or reactive derivatives thereof. For example, there is described in WO 2006/121778 a process for the production of a lower alkyl ester of a lower aliphatic carboxylic acid by carbonylating under substantially anhydrous conditions a lower alkyl ether, such as dimethyl ether, with carbon monoxide in the presence of a mordenite or ferrierite catalyst.

It would be desirable to improve the carbonylation catalytic activity of mordenite and/or its selectivity to carbonylation products in carbonylation processes, and, in particular, in the carbonylation of methanol and/or the ester and ether derivatives thereof to produce acetic acid and/or methyl acetate.

It has now been found that in carbonylation reactions which employ mordenite as catalyst, improved catalytic performance can be achieved by the use of a mordenite which has been subjected to a desilication treatment.

Accordingly, the present invention provides a process for the production of at least one of acetic acid and methyl acetate by the carbonylation of a carbonylatable reactant selected from methanol, methyl acetate and dimethyl ether with carbon monoxide in the presence of a catalyst, which catalyst is a desilicated mordenite.

The structure of mordenite is well known and is defined, for example, in The *Atlas of Zeolite Framework Types* (C. Baerlocher, W. M. Meier, D. H. Olson, 5$^{th}$ ed. Elsevier, Amsterdam, 2001). The web-based version (http://www.iza-structure.org/databases/) is a compendium of topological and structural details about zeolites including mordenite.

Mordenite can be obtained commercially or it may be synthesised. Commercially available forms of mordenite include the sodium form, the acid form and the ammonium form.

The mordenite which is to be subjected to the desilication treatment will hereinafter be referred to as the 'mordenite precursor'.

The mordenite precursor may have a silica:alumina ratio of at least 12:1, such as in the range 12 to 250:1. Suitably, the silica:alumina ratio of the mordenite precursor is in the range 20 to 100:1, for example, in the range 25 to 60:1.

Methods for desilication of zeolites are known in the art and result in the preferential removal of silicon from a zeolite framework. The method by which the mordenite precursor is desilicated to produce the desilicated mordenite for use as catalyst in the process of the present invention may be any desilication method known in the art. Suitably, the mordenite precursor is desilicated by treatment with an aqueous solution of a base. Suitable bases include alkali metal hydroxides and alkaline earth metal hydroxides. Preferred alkali metal hydroxides are sodium hydroxide and potassium hydroxide. Typically, the pH of the aqueous base solution is 8 or above. Suitable concentrations of alkali or alkaline earth metal hydroxide are 0.01 M to 1.0 M.

The extent of desilication is dependent upon, the concentration of the base, temperature of treatment and the length of time the treatment is continued. With solutions of 0.01 M to 1.0 M, effective desilication can be obtained at temperatures in the range 0 to 100° C., for a duration of 5 minutes to 10 hours. Moderate temperatures in the range 50 to 75° C. are preferred.

Following the base treatment, the desilicated mordenite is filtered off and washed with water to remove excess base and then dried. The desilicated mordenite may be used as is in the process of the present invention. Alternatively, the H-form of the desilicated mordenite may be prepared, for example, by converting it to the ammonium form followed by calcination of the ammonium form.

In a typical desilication treatment, sodium hydroxide solution (0.2 M) is added to a sample of H-mordenite of silica:alumina ratio of 15 to 60:1 in a reaction vessel and heated at a temperature in the range of 60 to 70° C. for a duration of 10 to 45 minutes. Subsequently, the reaction is quenched and cooled, for example, by submersion of the vessel in an ice-water mixture, followed by filtration and washing with deionised water. After filtration and washing, the mordenite is dried and calcined. Drying is typically carried out at about 110° C. The treatment of H-mordenite with sodium hydroxide provides the sodium form of the desilicated mordenite. The ammonium form of the desilicated mordenite can be prepared by exchanging the sodium form with an aqueous solution of an ammonium salt, filtering, and drying. Calcining the resulting desilicated ammonium mordenite at temperatures of, for example, 450 to 550° C. results in a desilicated H-mordenite.

Desilicated mordenites are used as the catalyst in the process of the present invention.

The silica:alumina ratio of the desilicated mordenite catalyst may be at least 10:1, for example, in the range 10 to 250:1, suitably in the range 15 to 100:1, such as in the range 25 to 60:1 and more suitably, in the range 15 to 40:1.

Suitably, the desilicated mordenite catalysts for use in the process of the present invention have silica:alumina ratios in the range 15 to 40:1 and are prepared from mordenite precursors which have silica:alumina ratios in the range 20 to 50:1.

In a preferred embodiment, the desilicated mordenite catalyst is prepared from a mordenite precursor which is a dealuminated mordenite.

The term 'dealumination' as used herein and throughout refers to the removal of aluminium from mordenite and includes the removal of framework and surface aluminium. Dealumination methods are known in the art and include treatment of zeolites with steam and/or acid leaching. For example, U.S. Pat. No. 3,551,353 describes a process for the dealumination of mordenite by contacting steam and mineral acid in alternate steps and U.S. Pat. No. 5,238,677 describes a process for the dealumination of a zeolite having the structure of mordenite by contacting the zeolite with a dicarboxylic acid and steaming.

Suitably, a dealuminated mordenite to be used as the mordenite precursor may be prepared by contacting a mordenite with steam or a mixture of an inert gas and steam at a temperature of at least 400° C. such as 400 to 600° C. The extent to which dealumination occurs will depend on the temperature at which steaming is carried out, the duration of the steaming and the concentration of steam the mordenite is exposed to. Typically, the steam treatment time is at least about 1 hour, preferably at least 3 hours.

Although mordenite may be dealuminated by treatment with either a mineral acid or with steam, it is preferred to use a combination of the two treatments. Thus, the steam treatment may be, and is preferably, followed by treatment with a mineral acid. Treatment with the mineral acid will remove extra framework aluminium generated during the steaming. Suitable mineral acids include hydrochloric acid and nitric acid. Typically the concentration of the acid will be in the range 0.5 M to 2.0 M. The acid treatment is continued for a length of time to remove essentially all of the extra framework aluminium from within the mordenite channels. Generally, for acid concentrations of 0.5 M to 2.0 M and at a temperature in the range 25 to 100° C., a duration of 1 to 5 hours is usually sufficient. The acid treated mordenite may then be filtered and washed with deionised water to neutral pH.

Prior to steaming, it is preferred to partially load the mordenite with a univalent metal. The univalent metal may be, for example, a metal belonging to Group 1 or Group 11 of the Periodic Table of Elements. The Group 1 metals are lithium, sodium, potassium, rubidium, cesium and francium. Of these, lithium, sodium and potassium are preferred, especially preferred is sodium. The Group 11 metals are silver, copper and gold. Silver is a preferred Group 11 metal.

Techniques for loading metals onto mordenites are well known, and include, for example, the methods of impregnation and ion-exchange. The univalent metal may be loaded onto the mordenite by either impregnation or ion-exchange. To achieve partial loading of the univalent metal, the molar amount of univalent metal loaded onto the mordenite should be less than the molar amount of aluminium present in the mordenite.

Optionally, prior to treatment with steam, the metal loaded mordenite may be calcined. Calcination is preferred where the mordenite (prior to partial loading with metal) was in the ammonium form. Calcination may be carried out at high temperature, such as at least 400° C., for several hours in air or an inert gas to remove ammonia and convert the ammonium ions to hydrogen ions.

Alternatively, any other known method of dealumination may be used. Suitable methods include treatment with a hexafluorosilicate salt such as alkali metal hexafluorosilicates and ammonium hexafluorosilicate. Suitable procedures are described, for example, in Garralon et al. Zeolites 8 (1988) 268.

Dealumination increases the silica:alumina ratio of a mordenite. Generally, the increase in the silica:alumina ratio will be in the range 5 to 100%.

Preferably, the silica:alumina ratio of a dealuminated mordenite precursor is in the range 25 to 50:1, for example, in the range 25 to 40:1.

A mordenite precursor which has been dealuminated may be in the H-form or in the ammonium form.

For use as catalyst in the process of the present invention, a dealuminated mordenite precursor is subjected to a desilication treatment to produce a desilicated mordenite.

Suitably, the catalyst for use in the process of the present invention is a desilicated mordenite in the H-form. Preferably, the catalyst for use in the process of the present invention is a desilicated mordenite which is dealuminated. More preferably, the catalyst is the H-form of a dealuminated desilicated mordenite.

The catalyst may be employed in the process of the present invention in any suitable form such as powders, pellets or other forms of extrudates.

The catalyst may be combined with a binder material. Preferably, the catalyst to be combined with a binder is dealuminated. Any suitable binders may be employed. Particularly useful binders are inorganic oxide materials such as one or more of the group selected from silica, alumina, silica-alumina, magnesium silicate and magnesium aluminium silicate, preferably, alumina or silica-alumina. Examples of suitable aluminas include boehmite type alumina and gamma-alumina.

Preferably, a binder is a refractory inorganic oxide such that the inorganic oxide is stable at high temperature, and, in particular is stable at temperatures which may be employed in calcination of the catalyst, such as a temperature of at least 400° C., for example, a temperature in the range 400 to 550° C.

Suitable binders may be mesoporous, for example inorganic oxides having a mesoporosity in the range 1 to 500 $m^2/g$. By mesoporosity is meant the sum of the total surface area of mesopores and the external surface area of the binder as measured by nitrogen BET. A mesopore is a pore having a diameter in the range 2 to 50 nanometers.

Preferably, mesoporous binders will also have low microporosity, such as a microporosity in the range 1 to 100 $m^2/g$, preferably in the range 1 to 10 $m^2/g$. By microporosity is meant the sum of the total surface area of micropores and the external surface area of the binder as measured by nitrogen BET. A micropore is a pore having a diameter of less than 2 nanometers.

Suitably, a binder may be present in an amount in the range of 10% to 80% by weight of the catalyst, preferably, in the range of 20% to 65% by weight of the catalyst, and, more preferably, in an amount in the range 35 to 65% by weight of the catalyst.

Suitably, the catalysts for use in the process of the present invention, and, in particular, dealuminated catalysts, may be combined with a binder which is a refractory inorganic oxide selected from one or more of silica, alumina and silica-alumina, which inorganic oxide is mesoporous, and preferably, an inorganic oxide having a mesoporosity in the range 50 to 500 m2/g.

In the process of the present invention, methanol and/or a reactive derivative thereof is carbonylated with carbon monoxide. Reactive derivatives of methanol which may be used as an alternative to, or in addition to methanol, include methyl acetate and dimethyl ether. A mixture of methanol and a reactive derivative thereof, for example a mixture of methanol and methyl acetate, may be employed. Where dimethyl ether is the carbonylatable reactant, it may be generated in-situ from any suitable source, such as dimethyl carbonate. For example, liquid dimethyl carbonate may be contacted with gamma-alumina to decompose the dimethyl carbonate to dimethyl ether and carbon dioxide.

Depending on the nature of the carbonylatable reactant used, the process of the present invention may be carried out under hydrous or substantially anhydrous conditions.

Preferably, where methyl acetate is used as the carbonylatable reactant, the process is carried out in the presence of water. Water may be present in the feed at a molar ratio of methyl acetate:water in the range 50:1 to 2:1.

Where the carbonylatable reactant is dimethyl ether, water has been found to inhibit the carbonylation process, thus it is preferred that when using dimethyl ether as a reactant, the process is carried out under substantially anhydrous conditions. By 'substantially anhydrous' is meant that, in the process, water is kept as low as is feasible. To accomplish this, the dimethyl ether and carbon monoxide reactants (and catalyst) are preferably dried prior to introduction into the process. However, small amounts of water may be tolerated without adversely affecting the formation of methyl acetate product. Suitably, water may be present in an amount of less than 2.5 wt %, for example, less than 0.5 wt % relative to the amount of dimethyl ether.

The purity of the carbon monoxide used is not deemed to be especially critical although it is desirable to use gas mixtures in which carbon monoxide is the main component. The presence of small amounts of impurities such as nitrogen and the noble gases can be tolerated. The carbon monoxide may be used in admixture with hydrogen. Suitably, the ratio of $CO:H_2$ is in the range 1:3 to 15:1 on a molar basis, such as 1:1 to 10:1. For example, mixtures of carbon monoxide and hydrogen as produced by the reforming or partial oxidation of hydrocarbons (synthesis gas) may also be used in the process of the present invention.

The process of the present invention is preferably carried out by passing methanol vapour and/or dimethyl ether vapour and carbon monoxide gas, optionally in the presence of hydrogen, through a fixed or fluidised bed of the catalyst maintained at the desired temperature and pressure.

The process may suitably be carried out at a temperature in the range of 100° C. to 400° C., such as 150 to 350° C.

The process may be carried out at a pressure in the range 1 to 100 barg, such as 10 to 100 barg.

The molar ratio of carbon monoxide to carbonylatable reactant is suitably in the range 1:1 to 99:1, such as 1:1 to 60:1.

Hydrogen may be present in the process, and may be present at a partial pressure of at least 0.1 barg, such as 1 to 30 barg.

The Gas Hourly Space Velocity (GHSV) is suitably in the range 500 to 40,000 $h^{-1}$, such as 2000 to 10,000 $h^{-1}$.

Prior to use in the process, the catalyst is activated by, for example, by subjecting it to elevated temperature for at least one hour under flowing nitrogen, carbon monoxide or hydrogen.

If desired, the carbonylatable reactant may be contacted with a bed of alumina or corundum immediately before the bed of catalyst.

Preferably, the process of the present invention is carried out substantially in the absence of halides, such as iodide. By substantially is meant that the halide content, such as the iodide content of the feed gases and catalyst are less than 500 ppm and preferably less than 100 ppm.

The process may be carried out either as a fixed bed, fluid bed or moving bed process.

The process may be operated as either a continuous or a batch process, preferably as a continuous process.

The product of the process is acetic acid and/or methyl acetate. Where the carbonylatable reactant is methanol, the carbonylation product is acetic acid but methyl acetate may also be produced, depending on the extent of carbonylation.

Where the carbonylatable reactant is dimethyl ether the primary product of the process is methyl acetate but small amounts of acetic acid may also be produced.

The acetic acid produced by the process of the present invention can be removed in the form of a vapour and thereafter condensed to a liquid. The acetic acid can be subsequently purified using conventional techniques, such as distillation.

Where methyl acetate is a product of the process, at least some may be recovered from the carbonylation reaction products and sold as such and/or recycled to the carbonylation reactor and/or at least a portion may be recovered and used as such as a feedstock for other chemical processes, and/or at least a portion of it may be hydrolysed to acetic acid using known techniques such as reactive distillation in the presence of an acid catalyst.

The invention will now be illustrated with reference to the following Examples.

EXAMPLE 1

Catalyst Preparation

Catalyst A: Desilicated Dealuminated H-Mordenite

The mordenite precursor used to prepare Catalyst A was a dealuminated H-mordenite.

The dealuminated H-mordenite was prepared from ammonium mordenite by loading with univalent metal, calcining, steaming and treating with a mineral acid.

50 g of ammonium mordenite (CBV21A ex Zeolyst International; silica:alumina ratio of 20:1) was mixed with 3.02 g of $NaNO_3$ (35.5 mmol) in 120 ml deionised water and stirred for 16 hours at room temperature. The water was then removed en vacuo and the resulting solid dried in an oven at a temperature of 110° C. for 20 hours and then calcined at 500° C. for 3 hours in static air to produce a H-mordenite partially loaded with sodium.

20 g of the sodium loaded H-mordenite was secured in a quartz tube packed with 15-20 cm of Raschig glass rings. Nitrogen (80 $cm^3$ $min^{-1}$) was fed into the tube heated to 500° C. using the temperature program:ambient temperature to 90° C. over 10 min, held at 90° C. for 30 min, heated to 110° C. over 10 min, held at 110° C. for 30 min, then heated to 500° C. over 60 minutes and held at that temperature for 4 hours. At 500° C., steam was generated by feeding deionised water (1 ml $min^{-1}$) into the tube for a period of 4 hours after which the flow of water was ceased. The quartz tube was then cooled to ambient temperature under a flowing nitrogen atmosphere.

20 g of the steam treated mordenite was then treated with an aqueous solution of HCl (200 ml, 1M) at 80° C. for 1 hour. The solution was filtered and the solid was washed with excess deionised water to remove all trace of chloride ions from the solid and then dried in an oven at a temperature of 110° C. for 20 hours. The dried solid, dealuminated H-mordenite, was analysed by inductively coupled plasma atomic emission spectrometry (ICP-OES) and had a silica: alumina ratio of 35:1.

The dealuminated H-mordenite was then desilicated by treatment with sodium hydroxide solution as follows.

10 g of dealuminated mordenite was treated with an aqueous solution of NaOH (300 ml, 0.2M) at 65° C. for 0.5 hours.

The solution was filtered and the solid washed with excess deionised water and dried in an oven at a temperature of 110° C.

8.2 g of the dried solid was exchanged three times with an aqueous solution of $NH_4NO_3$ (82 ml, 1M) at 80° C. for 1 hour. After the third exchange the solid was washed with excess deionised water, dried in an oven at a temperature of 110° C. for 20 hours and then calcined at 500° C. for 3 hours in static air. The calcined solid, dealuminated desilicated H-mordenite was analysed by ICP-OES and had a silica:alumina ratio of 29:1.

Catalyst B: H-Mordenite 10 g of ammonium mordenite of silica:alumina ratio of 20 (CBV21A ex Zeolyst International) was calcined at 500° C. for 3 hours in static air to obtain H-mordenite.

Catalyst C: Dealuminated H-Mordenite

A dealuminated H-mordenite was prepared in accordance with the method used in the preparation of Catalyst A except that the amounts were varied as follows (i) 8 g of mordenite was subjected to treatment with steam and (ii) 8 g of the steam treated mordenite was treated with 80 ml HCl. ICP-OES analysis of Catalyst C showed that its silica:alumina ratio was 37:1.

Catalyst D: Desilicated H-Mordenite

Mordenite was desilicated by treatment with sodium hydroxide solution as follows.

40 g of ammonium mordenite (CBV21A ex Zeolyst International; silica:alumina ratio of 20:1) was treated with an aqueous solution of NaOH (1200 ml, 0.2M) at 65° C. for 0.5 hours. The solution was filtered and the solid washed with excess deionised water and then dried in an oven at a temperature of 110° C. The dried solid (desilicated mordenite) was then converted to the H-form as follows.

10 g of the desilicated mordenite was exchanged three times with an aqueous solution of $NH_4NO_3$ (100 ml, 1M) at 80° C. for 1 hour. After the third exchange the solid was washed with excess deionised water, dried in an oven at a temperature of 110° C. for 20 hours and then calcined at 500° C. for 3 hours in static air. The calcined solid, desilicated H-mordenite was analysed by ICP-OES and had a silica:alumina ratio of 19:1.

Carbonylation Reactions Using Catalysts A to D

A Hastelloy reactor tube was packed with 0.6 ml catalyst (particle size 250 to 500 microns) and 0.2 g of a pre-bed of gamma alumina. The catalyst was heated by means of an electrical heating jacket. The reactor and heating jacket were housed in a cabinet maintained at a 130° C. The reactor was heated at atmospheric pressure to 130° C. under a flow of nitrogen at which point a gaseous mixture of 80 mol % carbon monoxide and 20 mole % hydrogen was introduced into the reactor at a flow rate (GHSV) of 5000 per hour. The reactor was pressurised to 20 barg, heated to a temperature of 300° C. and maintained under these conditions for 2 hours. The carbonylation reaction was then started by feeding liquid dimethyl carbonate into the reactor to provide a gas feed comprising 76 mole % carbon monoxide, 19 mole % hydrogen and 5 mole % dimethyl ether. The reaction was allowed to continue for 100 hours under conditions of 300° C., 20 barg, and a gas hourly space velocity (GHSV) of 5000 $h^{-1}$. A constant flow of reaction off-gases was taken, let down to atmospheric pressure at a temperature of 130° C. and passed to a gas chromatograph for analysis of acetyls products (acetic acid and methyl acetate). From the gas chromatography analysis of the reactor effluent for methyl acetate and acetic acid the space time yield (STY) of acetyls products was calculated as the molar equivalent weight of acetic acid corresponding to the sum of the methyl acetate and acetic acid produced expressed as grams of acetic acid per hour per liter of catalyst. The results are given in Table 1.

TABLE 1

| | Acetyls STY (g/l/hr) | | |
|---|---|---|---|
| Catalyst | TOS = 10 h | TOS = 20 h | TOS = 30 h |
| Catalyst A | 403 | 186 | 116 |
| Catalyst C | 130 | 110 | 103 |
| Catalyst D | 144 | 100 | 78 |
| Catalyst B | 111 | 73 | 54 |

TOS = time on stream

The results in Table 1 clearly show that in respect of the dealuminated catalysts, Catalysts A and C, the desilicated Catalyst A is a more effective carbonylation catalyst than the non-desilicated Catalyst C. Similarly, for the non-dealuminated catalysts, Catalysts D and B, desilicated Catalyst D exhibits greater carbonylation catalytic activity than the non-desilicated Catalyst B.

EXAMPLE 2

Catalyst Preparation

Catalyst E 50 g of H-mordenite (ex BASF; silica:alumina ratio of 40.5:1) was treated with an aqueous solution of NaOH (1500 ml, 0.2M) at 65° C. for 0.5 hours. The solution was filtered and the solid washed with excess deionised water and dried in an oven at a temperature of 110° C. 35 g of the dried solid (desilicated mordenite) was exchanged three times with an aqueous solution of $NH_4NO_3$ (350 ml, 1M) at 80° C. for 1 hour. After the third exchange the solid was washed with excess deionised water and dried overnight in an oven at a temperature of 110° C.

30 g of the desilicated material prepared above and 15 g of alumina binder (ex Sasol, Pural SCF) were combined by gently milling together in a Büchi powder drying flask until a free flowing powder was produced. The powder was then blended on a rotor evaporator at a speed of 100 r.p.m. for 1 hour at ambient temperature and pressure and then calcined for 3 hours at 500° C. under an atmosphere of static air.

Catalyst F 30 g of H-mordenite (ex BASF; silica:alumina ratio of 40.5:1) and 15 g of alumina binder (ex Sasol, Pural SCF) were combined by the method described in Catalyst E above.

Carbonylation Reactions Using Catalysts E and F

Prior to use as catalysts in the carbonylation of dimethylether (DME) with carbon monoxide, Catalysts E and F were compacted at 10 tonnes in a 13 mm die set using a pneumatic press, and crushed and sieved to a particle size fraction of 125 to 160 microns.

The carbonylation reactions were carried out in a pressure flow reactor unit consisting of 16 identical reactors of the type described in WO 2005063372. Each reactor had an internal diameter of 9.2 mm and the centre of each reactor was fitted with a tube of diameter 3.2 mm into which a thermocouple was placed.

A 10 cm corundum bed of sieve fraction of 125-160 µm was placed in each reactor. On a dry mass basis (determined by loss on ignition of the catalyst measured by heating the catalyst from room temperature to 600° C. at a ramp rate of 30° C. per minute), 1.948 g (approximately 3 ml) of a catalyst diluted with 3 ml of corundum was placed on top of the corundum bed. The diluted catalyst was covered by 11 cm bed of corundum of particle size of 125-160 microns. 1 g of gamma-alumina (ex BASF SAS 250) of pellet size 125-160 microns was placed on top of the corundum, to a depth of 2 cm.

The reactors were pressurised to a reaction pressure of 70 bar with a gas feed of a 4:1 molar ratio of carbon monoxide: hydrogen at a flow rate of 12 L/h per reactor. The reactors were then heated at 1° C./min to a holding temperature of 220° C., where they were held for a dwell time of 3 hours. The temperature was then ramped to 300° C. at 1° C./min, again followed by a dwell time of 3 hours. The gas feed was then changed to a mixture of carbon monoxide, hydrogen, dimethyl ether, argon and methyl acetate at a molar ratio of 70.8:17.7:6:5:0.5 respectively at a total flow rate of 12 L/h per reactor, with a dimethyl ether vapour feed rate of 0.72 L/h per reactor and a methyl acetate vapour feed rate of 0.06 L/h per reactor. Nitrogen was introduced at a variable rate of 0-150 ml/min to equalise the pressure swings between the 16 reactor exits. The exit stream from each reactor was periodically passed to a gas chromatograph to determine the concentration of reactants and carbonylation products. The reaction was allowed to continue for 263 hours under conditions of 300° C., 70 bar and a gas hourly space velocity (GHSV) of 4000/h.

From the gas chromatography analysis, the space time yield (STY) of acetyls products was calculated as the molar equivalent weight of acetic acid corresponding to the sum of the methyl acetate and acetic acid produced expressed as grams of acetic acid per hour per liter of catalyst. The acetyls product was predominantly methyl acetate. The results are given in Table 2.

TABLE 2

| Catalyst | Acetyls STY (g/l/hr) | | |
|---|---|---|---|
| | TOS = 50 h | TOS = 100 h | TOS = 140 h |
| Catalyst E | 238 | 277 | 294 |
| Catalyst F | 195 | 153 | 133 |

TOS = time on stream

The results in Table 2 clearly show that the catalyst which has been desilicated, Catalyst E is significantly more effective than the non-desilicated catalyst, Catalyst F.

EXAMPLE 3

Catalyst Preparation

Catalyst G: Dealuminated H-Mordenite 10 g of sodium mordenite (CBV10A ex Zeolyst International, silica:alumina ratio of 13) was dealuminated by treatment with aqueous HCl (200 ml, 1M) at 100° C. for 1 hour. The solution was filtered and the solid washed with excess deionised water and dried overnight in an oven at a temperature of 110° C. The dried solid (dealuminated mordenite) was analysed by ICP-OES and had a silica:alumina ratio of 29.5:1.

5 g of the dealuminated mordenite was exchanged three times with an aqueous solution of NH$_4$NO$_3$ (50 ml, 1M) at 80° C. for 1 hour. After the third exchange the solid was washed with excess deionised water, dried overnight in an oven at a temperature of 110° C. and then calcined at 500° C. for 3 hours in static air.

Catalyst H: Dealuminated H-Mordenite

Catalyst H of silica:alumina ratio of 34:1 was prepared by repeating the method used in the preparation of Catalyst G, except that 20 g of sodium mordenite was treated with 400 ml of 1.0 M aqueous HCl under reflux for 1 hour.

Catalyst I: Dealuminated Desilicated H-Mordenite 10 g of dealuminated mordenite (Catalyst H) was desilicated by treatment with an aqueous solution of NaOH (300 ml, 0.2M) at 65° C. for 0.5 hours. The solution was filtered and the solid washed with excess deionised water and dried in an oven at a temperature of 110° C. The dried dealuminated desilicated mordenite was exchanged three times with an aqueous solution of NH$_4$NO$_3$ (100 ml, 1M) at 80° C. for 1 hour. After the third exchange the solid was washed with excess deionised water, dried in an oven at a temperature of 110° C. for 20 hours and then calcined at 500° C. for 3 hours in static air. The calcined solid (dealuminated desilicated H-mordenite) was analysed by ICP-OES and had a silica:alumina ratio of 29.5:1.

Carbonylation Reactions Using Catalysts G to I

The carbonylation reactions were carried out in a pressure flow reactor unit consisting of 16 identical parallel isothermal co-current tubular reactors of the type described in, for example, WO2006107187. The reactors were arranged in 4 blocks of 4 reactors, each block having an independent temperature control. Each reactor had a metal sinter of pore size 20 micrometers onto which was placed 0.072 g of a catalyst pressed and sieved to 100-160 μm (approximately 100 μL) to give a gas hourly space velocity (GHSV) of 4000 h$^{-1}$. 100 μL of gamma-alumina (SAS200 ex BASF) crushed and sieved to 100-160 μm was placed on top of the catalyst bed. Carborundum was placed on top of the gamma-alumina bed. Each catalyst was heated at atmospheric pressure to 300° C. at a ramp rate of 5° C./min. under nitrogen at a flow rate of 3.1 mL/min. per reactor and held at 300° C. for 1 hour. Nitrogen was then replaced by a gaseous feed of 77.6 mol % carbon monoxide, 19.3 mol % hydrogen and 3.1 mol % He at a flow rate of 6.1 ml/min. per reactor. The pressure was then raised to 60 barg and left to equilibrate for two hours. A gas feed comprising 69.7 mol % carbon monoxide, 17.5 mol % hydrogen, 2.8 mol % He, 5 mol % carbon dioxide and 5 mol % dimethyl ether was introduced into each reactor at a flow rate of 6.7 ml/min. per reactor. The reaction was continued for 160 hours. The exit stream from each reactor was periodically passed to a gas chromatograph to determine the concentration of reactants and carbonylation products.

From the gas chromatography analysis, the space time yield (STY) of acetyls products was calculated as the molar equivalent weight of acetic acid corresponding to the sum of the methyl acetate and acetic acid produced expressed as grams of acetic acid per hour per liter of catalyst. The acetyls product was predominantly methyl acetate. The results are given in Table 3.

TALBE 3

| Catalyst | Acetyls STY (g/l/hr) | | |
|---|---|---|---|
| | TOS = 50 h | TOS = 100 h | TOS = 140 h |
| Catalyst I | 308 | 217 | 189 |
| Catalyst G | 54 | 46 | 41 |
| Catalyst H | 58 | 47 | 42 |

TOS = time on stream

Although Catalysts I and G have the same silica:alumina ratio, the results in Table 3 clearly show that Catalyst I (the desilicated catalyst) has significantly improved carbonylation catalytic activity compared to Catalyst G (the non-desilicated catalyst).

The invention claimed is:

1. A process for the production of at least one of acetic acid and methyl acetate comprising carbonylating a carbonylatable reactant selected from methanol, methyl acetate and dimethyl ether with carbon monoxide in the presence of a catalyst, which catalyst is a desilicated mordenite.

2. A process according to claim 1 wherein the desilicated mordenite is dealuminated.

3. A process according to claim 1 wherein the desilicated mordenite is in the hydrogen form.

4. A process according to claim 1 wherein the desilicated mordenite has a silica:alumina ratio in the range 15 to 40:1.

5. A process according to claim 1 wherein the desilicated mordenite is prepared by treating a mordenite precursor with an aqueous solution of an alkali metal hydroxide or an alkaline earth metal hydroxide.

6. A process according to claim 5 wherein the mordenite precursor is a dealuminated mordenite which has been prepared by partially loading a mordenite with a univalent metal, treating the partially loaded metal mortenite with steam and subsequently treating the steamed mordenite with a mineral acid.

7. A process according to claim 1 wherein the catalyst is combined with a binder.

8. A process according to claim 7 wherein the binder is an inorganic oxide.

9. A process according to claim 7 wherein the catalyst is dealuminated.

10. A process according to claim 1 wherein the carbonylatable reactant is dimethyl ether.

11. A process according to claim 10 wherein the carbonylatable reactant is dimethyl ether and water is present in an amount of less than 2.5 wt % relative to the amount of dimethyl ether.

12. A process according to claim 1 wherein the process is carried out in the presence of hydrogen.

13. A process according to claim 1 wherein the process produces methyl acetate.

14. A process according to claim 13 wherein at least a portion of the methyl acetate is hydrolysed to acetic acid.

15. A process according to claim 1 wherein the process is operated as a continuous process.

* * * * *